United States Patent [19]

Nielson et al.

[11] Patent Number: 4,760,444
[45] Date of Patent: Jul. 26, 1988

[54] MACHINE VISUAL INSPECTION DEVICE AND METHOD

[75] Inventors: Paul C. Nielson, N. Andover; Wolfgang Kaufman, Northampton, both of Mass.

[73] Assignee: CSD International, Inc., Shelburne Falls, Mass.

[21] Appl. No.: 76,391

[22] Filed: Jul. 22, 1987

[51] Int. Cl.4 ............................................. H04N 7/18
[52] U.S. Cl. .................................. 358/101; 358/106; 358/107; 358/903; 364/552
[58] Field of Search ................. 358/101, 106, 107, 93, 358/903; 364/552

[56] References Cited

U.S. PATENT DOCUMENTS

| | | | |
|---|---|---|---|
| 3,872,243 | 3/1975 | Soames | 358/107 |
| 4,246,606 | 1/1981 | Yoshida | 358/106 |
| 4,319,272 | 3/1982 | Henry | 358/107 |
| 4,344,146 | 8/1982 | Davis | 364/552 |
| 4,417,274 | 11/1983 | Henry | 358/107 |
| 4,521,807 | 6/1985 | Werson | 358/106 |
| 4,556,902 | 12/1985 | Krufka | 358/106 |
| 4,570,180 | 2/1986 | Baier | 358/101 |
| 4,589,140 | 5/1986 | Bishop | 358/106 |
| 4,670,788 | 6/1987 | Ozaki | 358/101 |
| 4,706,120 | 11/1987 | Slaughter | 358/101 |

Primary Examiner—Howard W. Britton
Attorney, Agent, or Firm—Leonard M. Quittner

[57] ABSTRACT

A visual inspection device is disclosed in which a workpiece to be inspected is set onto a holding fixture in a defined position, the holding fixture having a fixed, crosshair target in a defined location on the fixture. The fixture is transported into one or more consecutive illuminated video scanned inspection fields having prepositioned therein a calibrated gray scale. The piece is then viewed for inspection by a video camera as an addressed data stream containing reflectance values and transmitted to a digitizer and a central processing unit. The inspection field of the data stream is shifted algorithmically such that the target is brought into alignment with and matches a target contained in a reference stream in memory. The data stream is further corrected algorithmically for ambient light by comparing the gray scale reflectance values in the inspection field to a reference gray scale in memory which has not been affected by ambient light. Variations in values cause rejection. Totalizing of rejection by address combinations is retained in memory and the inspection device is automatically shut down when defined rejection totals are reached.

18 Claims, 3 Drawing Sheets

MACHINE VISUAL INSPECTION DEVICE AND METHOD

CROSS-REFERENCE

There are no cross-references to nor are there any related applications.

FEDERALLY-SPONSORED RIGHTS

The invention herein was made without any Federal sponsorship or contribution.

BACKGROUND OF THE INVENTION

1. The Field of the Invention

The field of the invention relates to an improved machine visual inspection device and method which uses the technique of video scanning a workpiece to be inspected by video camera means which transmits signals from the video signal plate point or region array in the camera view or inspection field by line and time to a computer's central processing unit in which is stored a pre-scanned workpiece image in the format of a video array or reference field for comparison. The device is particularly useful in inspecting brushes of various kinds.

2. Description of the Prior Art

The prior art is best demonstrated by U.S. Pat. Nos. 3,872,243 (Mar. 18, 1975) to Soames, et. al.; 4,319,272 (Mar. 9, 1982) to Henry; 4,344,146 (Aug. 10, 1982) to Davis, et. al.; 4,417,274 (Nov. 22, 1983) to Henry; 4,521,807 (June 4, 1985) to Werson; 4,556,902 (Dec. 3, 1985) to Krufka and 4,589,140 (May 13, 1986) to Bishop, et. al. in which typical circuitry and protocol permit a workpiece to be inspected in a video scanned inspection field made up of discrete line and time addressable points or regions. The workpiece image being scanned receives a measured, defined light value or datum for each point or region in the field. A series of analogue signals are transmitted region, by region each incorporating a datum, in a defined order on a carrier to a digitizer. The addresses and data are then digitized and read into a central processing unit of a computer in which resides in memory a predetermined "correct" image having an identical type of light value for each address. A compare function resident in the central processing unit memory determines whether the transmitted image values and the stored image values match, or map and if they do not, within predefined parameters, a rejection means is activated. See also U.S. Pat. Nos. 3,902,811 (Sept. 2, 1975) to Altman, et. al.; 3,980,870 (Sept. 14, 1976) to Kawahara; 4,437,115 (Mar. 13, 1984) to Yoshida; 4,454,541 (June 12, 1984) to Suzuki, et. al.; 4,473,842 (Sept. 25, 1984) to Suzuki, et. al.; 4,479,145 (Oct. 23, 1984) to Azura, et. al.; 4,480,264 (Oct. 30, 1984) to Duschl; 4,492,476 (Jan. 8, 1985) to Miyazawa; 4,433,385 (Feb. 21, 1985) to DeGasperi; 4,576,48 (Mar. 18, 1986) to Pryor, and 4,606,635 (Aug. 19, 1986) to Miyazawa.

Reference is also made to FRGP/UM (Offeniegungsschrift) Nos. DE3417086A1, DE3501512 and European Pat. No. 0189067 to Zahoransky which in general terms show partial solutions to problems involving the inspection of brushes by unspecified camera imaging techniques and by photocells. Mechanical sensors taught in the Zahoransky patent are not applicable here.

U.S. Pat. No. 4,246,606 (Jan. 20, 1981) to Yoshida, utilizes a white standard installed in the inspection field to assist in the standardization of brightness and U.S. Pat. No. 4,570,180 (Feb. 11, 1986) to Baier, et. al., utilizes a gray scale in the inspection field for certain purposes not germane to the present invention.

The prior art is not responsive to the inevitable error effects that the reflectance values of ambient light have on the inspection field image. These often fluctuate randomly or by local lighting changes and reflectance errors cause improper rejection (or acceptance). The inspection is also not responsive to alignment errors which are inherently induced in workpiece transfer systems. These cause mismatching or mapping and, therefore, improper rejection (or acceptance).

SUMMARY OF THE INVENTION

The invention described herein is summarized as a machine visual inspection device and method of inspection, particularly useful in inspecting at high speed small workpieces, typified by tooth brushes. The completed unit is produced on an automatic production line wherein machining or forming takes place in discrete steps leading to a finished workpiece for inspection. Speeds of 80 brushes a minute are not unusual. The brush handle is first locked into a fixture which has a defined, exact positional relationship to a target, typically in the form of cross hairs situated thereon. The handle is then stuffed with bristles in tufts, the tufts adhered, shaped and trimmed and the finished brush inspected for properly shaped tufts, density of tuft, vertically and so-called "wild" bristles all of which have unique reflectance values. Each unit is accepted or rejected based on these values. To accomplish high production line speeds and also to create a sanitary atmosphere in which manufacture takes place the entire activity must be automatic.

We have found that two major errors are possible in the present state of the art: position misalignment of the viewed object in the inspection field with the reference object as stored in memory and the distortional effect on reflectance values created by ambient light. This must inevitably be present in the inspection field and significantly affects the transmitted reflectance values. The present invention eliminates these errors.

In manufacture, the fixture bearing its target and workpiece is transferred to one or more illuminated video inspection stations each having a video inspection field located thereat for scanning reflectance values of the workpiece and the target's location. Each inspection field has permanently situated in it at a defined location a defined calibrated gray scale, typically according to A.N.S.I. standards. The image of the scale, the workpiece and target are scanned together in the inspection field in two axes in the form of a defined stream of analogue signals addressed by location $(X_n, Y_n)$, in reality time $(X_n)$ and line $(Y_n)$, with a scanned reflectance value $(F_n)$ distorted by ambient light $(a)$ for each $(X_n, Y_n, F_n + a)$. The address/reflectance values $(X_1, Y_1, F_1 + a_1; X_2, Y_2, F_2 + a_2 \ldots X_n, Y_n, F_n + a_n)$ are generated sequentially (hereinafter the "data stream"), are multiplexed (if more than one inspection station is used), digitized and read into memory in the central processing unit of a computer which contains a standard image previously installed in memory as a reference stream which is also stated in address/reflectance value, $(X_{r1}, Y_{r1}, F_{r1}; X_{r2}, Y_{r2}, F_{r2}; \ldots X_{rn}, Y_{rn}, F_{rn})$ but with no ambient light distortion. The data stream also contains the target's data signals $(X_t, Y_t, F_t + a_t)$ and the data of the defined calibrated gray scale $(X_g,$ Yg, Fg+ag). A first correction for position is applied to each address in the data stream algorithmically by shifting the field target (Xt, Yt) and all other addresses together to align with the reference target (Xtr, Ytr) and, resultantly, all other addressed reference values (Xrn, Yrn, Frn), the central processing unit determining from coordinates in the X and Y axis what the position alignment algorithm is. A second correction to eliminate the effect of ambient light is applied to the data stream reflectance values (F) by comparing the values transmitted by the calibrated gray scale located in the inspection field (Fn) with the standard calibrated gray scale (no ambient light) stored as the reference (Fr). The ambient light correction (an) is found by gray comparisons and the correction is applied to the reflectance values in the data stream (Fn+a−an). If matching occurs within predefined parameters for reflectance at defined addresses, the inspected piece is accepted. If any value or group of values is not matched, a defect is deemed to have occurred and the workpiece stands to be rejected automatically. It should be obvious to one skilled in the art that one particular value (X, Y, F) in the data stream need not necessarily be determinative of defect, but that a cluster or neighborhood of values can be averaged or otherwise statistically manipulated to provide acceptance/rejection criteria.

The event of a particular error at a particular address or neighborhood of addresses can also be stored in memory and totalized within predefined parameters to create a rejection threshold, to shut the line down or generate a report. By this means a line operator can be informed by the central processing unit where specific production line corrections are required.

An object of the present invention is to ensure proper mapping of the data stream with the reference stream by eliminating positional errors caused by high speed inspection.

A further object is to provide a simple, accurate means of eliminating reflectance value errors created by ambient light generally present in an automatic visual inspection.

An additional object is to provide statistical means by which process or manufacturing errors may be found and corrected.

DESCRIPTION OF DRAWINGS

The present invention may be better understood by reference to the drawings wherein seven (7) figures are shown on three (3) sheets. The numbers shown on the drawings for the various parts of the invention are consistent throughout so that a number indicating a part in one drawing will indicate the same part in another drawing.

DESCRIPTION OF THE PREFERRED EMBODIMENT

The preferred embodiments are described as consisting of a visual inspection device and a method by which inspection is accomplished by means of the device.

A. The Device

Figure 1:
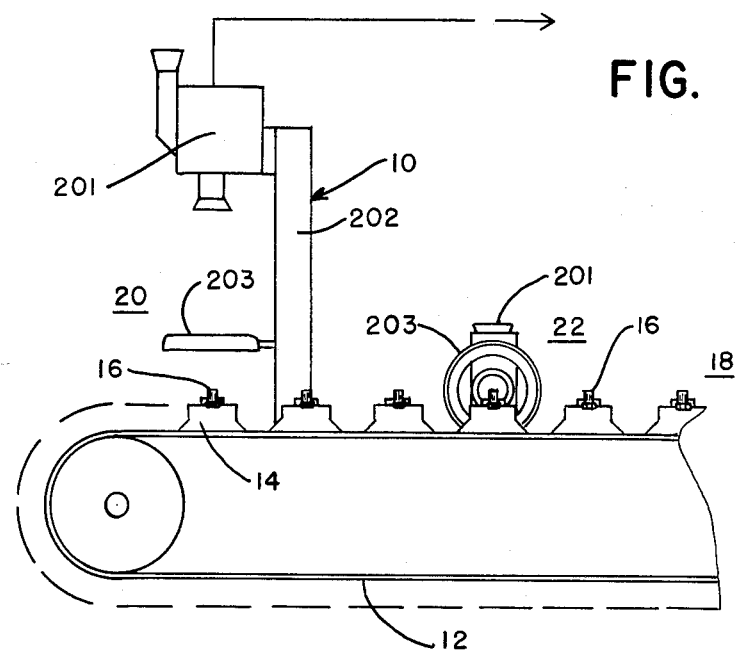
FIG. 1 shows a schematic view of a production line utilizing an automatic visual inspection system with video cameras positioned typically two (2) inspection stations.
Figure 2:
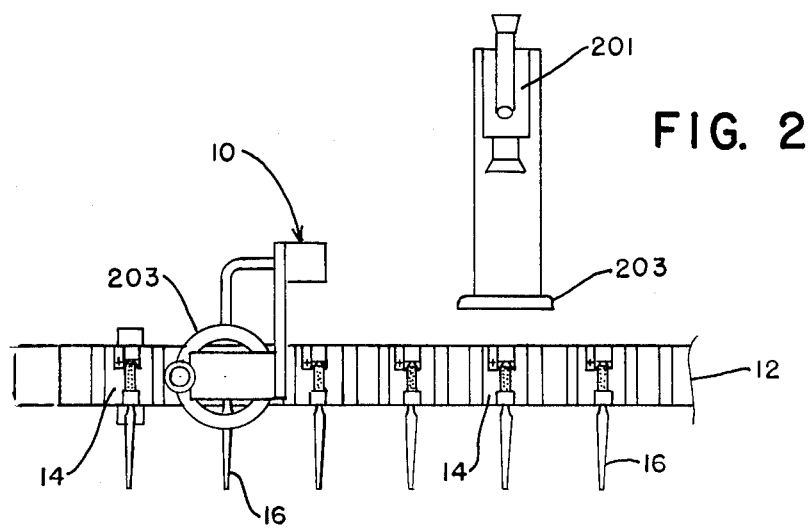
FIG. 2 shows a plan view of FIG. 1.
Figure 3:
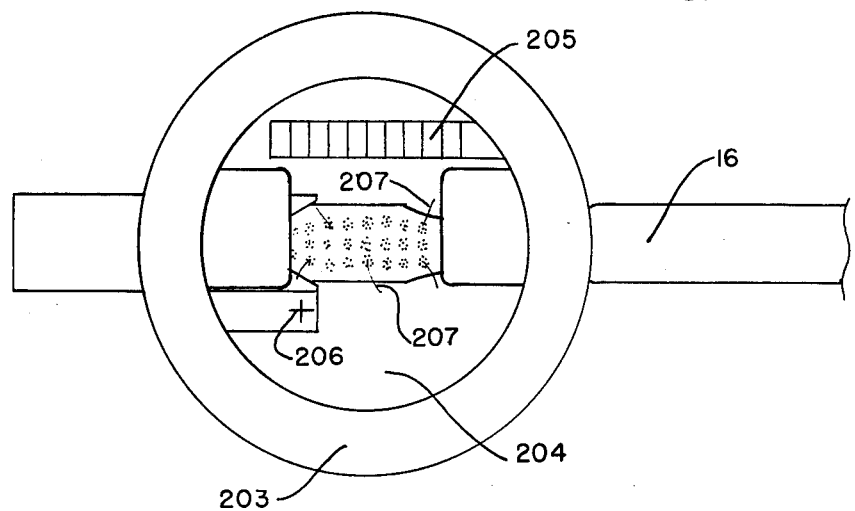
FIG. 3 shows a typical top view of an illuminated inspection field with target, gray scale and wild strands of a brush visible.
Figure 4:
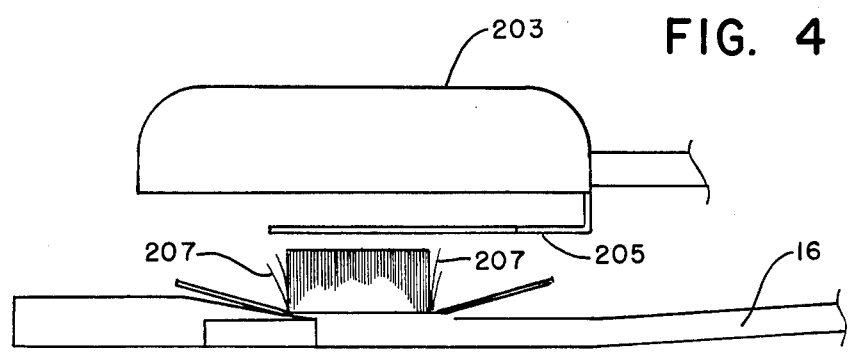
FIGS. 4 and 5 are side views of FIG. 3 and show wild strands similarly.
Figure 5:
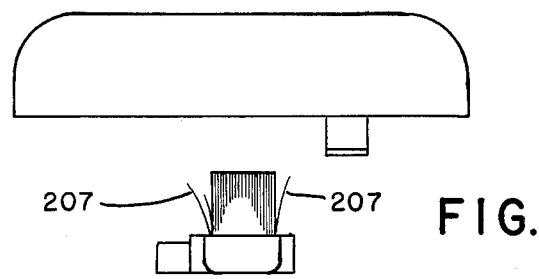
Figure 6:
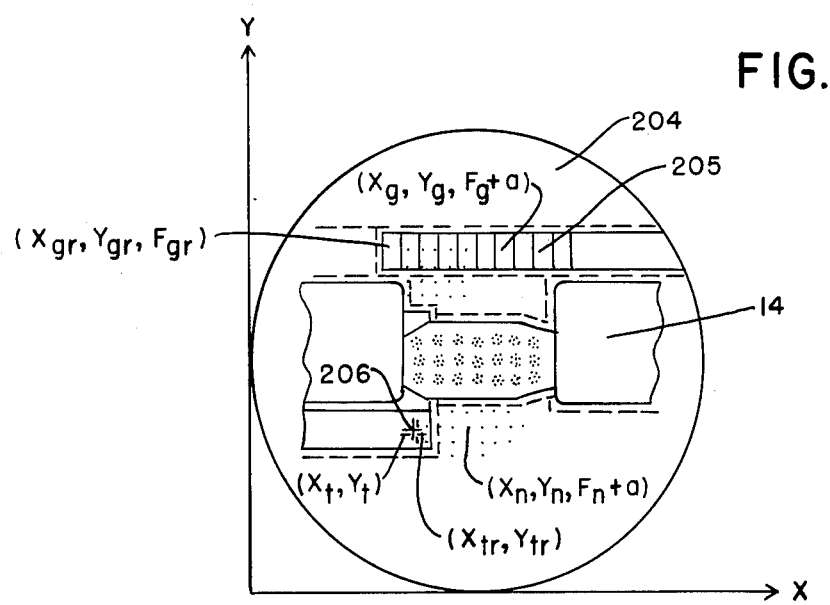
FIG. 6 is a theoretical view of an array of data superimposed on a reference array.
Figure 7:
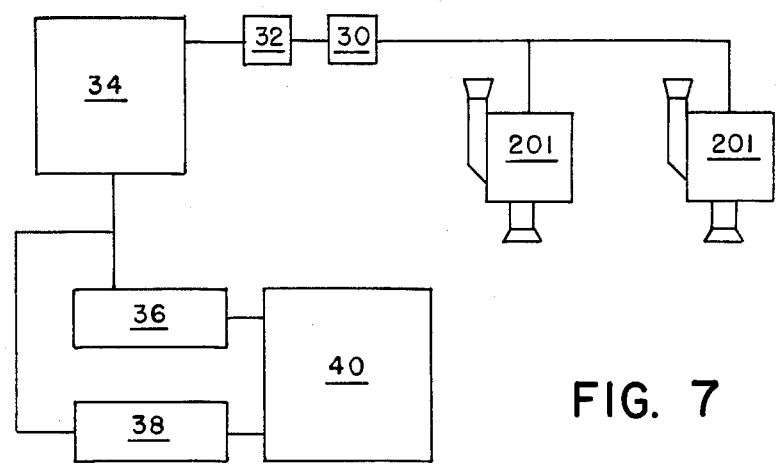
FIG. 7 is a block diagram of the essential components of the visual inspection system as they relate to each other.

The visual inspection device (10) comprises transport means (12) in the form of a production line conveyor, a holding/locking means (14) or fixture for holding a workpiece (16) to be worked and inspected, an area (18) in which manufacturing operations (not shown) may take place in progressive discrete steps, as for example by advancing the workpiece in stages through fabrication to inspection, and at least one inspection station (20) or additional ones (22) as required to complete the inspection. Each inspection station comprises a video camera (201) on a stand (202) which holds an illuminator (203) typically a fluorescent lamp in a circular configuration to illuminate the inspection field (204). In the inspection field is mounted in a fixed position a calibrated gray scale (205) typically an Eastman Kodak #152-2267 made visible in the inspection field. On each fixture is located so it is visible in the inspection field in a fixed, defined position a target (206), preferably in a cross-hair configuration. If more than one video camera is used, they are optionally connected to a multiplexer (30) to accept a data stream is generated consisting of addressed analogue signals carrying reflectance values to a digitizer (32) to digitize the signals. These are read into memory in the central processing unit (34) of a computer which can accept, store and compare the values of the data stream with the values of a predetermined reference stream also stored in memory. See FIG. 6. Rejection means (36) are fitted to the production line after the last inspection station to reject any work piece whose data values fall outside of predefined limits set for the reference values. For example, a wild bristle (207) will appear as a series of addressed points or regions with reflectance values at locations where different values should be. Accepting (38) is by default.

B. The Process

A workpiece, (16) having been mounted and locked on the transport means and worked to completion, is transported into an illuminated inspection field (204) and is viewed for inspection. Each region in the video array has an address (Xn, Yn) and a reflectance value (Fn). A series of signals signaling the addresses and values (X, Y, F) of the regions is transmitted in a data stream (optionally if more than one inspection station) to a multiplexer (30) which receives the signals from all the inspection stations installed (20, 22). The signals are then digitized (32) and read into memory in a central processing unit (34) and stored for correction and comparison. There the data stream is corrected algorithmically for address errors by first matching and aligning the target in the data stream to a reference target (See FIG. 6) in a reference stream resident in memory so that each address in the data stream is in exact correspondence with an address in the reference stream. As a next step, the data stream reflectance values are corrected by address algorithmically for ambient light variations by comparing the gray scale reflectance values transmitted in the data stream with stored calibrated gray scale values in the reference stream, to determine the difference therebetween and to apply a correction to each reflectance value in the data stream. Thereupon as a final step the data stream is compared with the reference stream and if any data stream values fall outside of those defined in the reference stream the workpiece is rejected (36) and the address, or neighborhood of addresses of the offending reflectance value or values is stored in memory. In this way repetitive production line errors may be analyzed statistically (40) and the production line automatically stopped or the errors reported out cumulatively. This permits the operator to find the source of production error exactly and correct it.

What is claimed is:

1. A machine visual inspection device for inspecting a work piece by video image means in combination comprising:
   a. a video camera attached to a stand which scans by reflectance values an illuminated inspection field containing the workpiece and in defined locations within the field a calibrated gray scale and a target;
   b. the video camera having scanning means for transmission of addressed reflectance values of the workpiece, the gray scale and the target as analogue signals which values are converted by digitizing means into a data stream of digital signals, which are read into memory in a central processing unit of a computer which has stored in said memory for comparison with the data stream a defined digitized reference stream comprising defined addresses and reflectance values for the workpiece, calibrated gray scale and target;
   c. the computer's memory having aligning means to align the data stream target with the reference target; and
   d. the computer's memory having comparison means whereby the stream's gray scale and reference streams gray scales may be compared finding their difference;
   e. the device having rejection means to reject the workpiece.

2. A machine visual inspection device for inspection a workpiece by video image means in combination comprising:
   a. A video camera attached to a stand which scans by reflectance values an illuminated inspection field containing the workpiece and in defined locations within the field a calibrated gray scale and a target;
   b. the video camera having scanning means for transmission of addressed reflectance values of the workpiece, the gray scale and the target as analogue signals which values are converted by digitizing means into a data stream of digital signals which are read into memory in a central processing unit of a computer which has stored in the said memory for comparison with the data stream a defined digitized reference stream comprising defined addresses and reflectance values for the workpiece, calibrated gray scale and target;
   c. the computer's memory having aligning means to align the data stream target with the reference target; and
   d. the device having rejection means to reject the workpiece.

3. A machine visual inspection device for inspecting a workpiece by video image means in combination comprising:
   a. A video camera attached to a stand which scans by reflectance values an illuminated inspection field containing the workpiece and in defined locations within the field a calibrated gray scale and a target;
   b. the video camera having scanning means for transmission of addressed reflectance values of the workpiece, the gray scale and the target as analogue signals which values are converted by digitizing means into a data stream of digital signals which are read into memory in a central processing unit of a computer which has stored in said memory for comparison with the data stream a defined digitized reference stream comprising defined addresses and reflectance values for the workpiece, calibrated gray scale and target;
   c. the computer's memory having comparison means whereby the data stream's gray scale and reference stream's gray scales may be compared finding their difference;
   d. the device having rejection means to reject the workpiece.

4. A machine visual inspection device for inspecting a brush by video image means in combination comprising:
   a. A machine visual inspection device for inspecting brushes by video image means in combination comprising:
   b. a video camera attached to a stand which scans by reflectance values an illuminated inspection field containing the brush and in defined locations within the field a calibrated gray scale and a target;
   c. the video camera having scanning means for transmission of addressed reflectance values of the brush, the gray scale and the target as analogue signals which values are converted by digitizing means into a data stream of digital signals which are read into memory in a central processing unit of a computer which has stored in said memory for comparison with the data stream a defined digitized reference stream comprising defined addresses and reflectance values for the brush, calibrated gray scale and target;
   d. the computer's memory having aligning means to align the data stream target with the reference target; and
   e. the computer's memory having comparison means whereby the data stream's gray scale and reference stream's gray scales may be compared finding their difference;
   f. the device having rejection means to reject the brush.

5. A machine visual inspection device as in claim 4 wherein the brush is a toothbrush.

6. A machine visual inspection device for inspecting a brush by video image means in combination comprising:
   a. A video camera attached to a stand which scans by reflectance values an illuminated inspection field containing the brush and in defined locations within the field a calibrated gray scale and a target;
   b. the video camera having scanning means for transmission of addressed reflectance values of the brush, the gray scale and the target as analogue signals which values are converted by digitizing means into a data stream of digital signals which are read into memory in a central processing unit of a computer which has stored in said memory for comparison with the data stream a defined digitized reference stream comprising defined addresses and reflectance values for the brush, calibrated gray scale and target;

c. the computer's memory having aligning means to align the data stream target with the reference target; and d. the device having rejection means to reject the brush.

7. A machine visual inspection device as in claim 5 wherein the brush is a toothbrush.

8. A machine visual inspection device for inspecting a brush by video image means in combination comprising:

a. A video camera attached to a stand which scans by reflectance values an illuminated inspection field containing the workpiece and in defined locations within the field a calibrated gray scale and a target;

b. the video camera having scanning means for transmission of addressed reflectance values of the brush, the gray scale and the target as analogue signals which values are converted by digitizing means into a data stream of digital signals which are read into memory in a central processing unit of a computer which has stored in said memory for comparison with the data stream a defined digitized reference stream comprising defined addresses and reflectance values for the brush, calibrated gray scale and target;

c. the computer's memory having comparison means whereby the data stream's gray scale and reference stream's gray scales may be compared finding their difference;

d. the device having rejection means to reject the brush.

9. A machine visual inspection device as in claim 8 wherein the brush is a toothbrush.

10. A process for video inspection of a workpiece locked on a target bearing fixture in an inspection field containing a calibrated gray scale comprising the steps of:

a. viewing the workpiece in a video inspection field containing the calibrated gray scale and target for reflectance values by video means;

b. transmitting the reflectance values of the workpiece, target and gray scale as addressed analogue signals in a data stream;

c. digitizing the data stream signals;

d. transmitting the digitized data stream to a central processing unit of a computer having a memory and storing the same;

e. correcting the addresses in the data stream by alignment algorithmically the target therein contained with a reference target in a reference stream contained in the memory;

f. correcting the reflectance value of the gray scale in the data stream by comparing it with its equivalent gray scale value in the reference stream and applying the correction to the reflectance values in the data stream;

g. comparing the corrected data stream reflectance values with the reference stream reflectance values;

h. rejecting the workpiece if reflectance values in the data stream do not fall with defined limits with the reference stream;

i. accepting the workpiece of the data stream reflectance values fall within the defined limits of the reference stream.

11. A process for video inspection of a workpiece locked on a target bearing fixture in an inspection field comprising the steps of:

a. viewing the workpiece in a video inspection field containing the target reflectance values by video means;

b. transmitting the reflectance values of the workpiece and target as addressed analogue signals in a data stream;

c. digitizing the data stream signals;

d. transmitting the digitized data stream to a central processing unit of a computer having a memory and storing the same;

e. correcting the addresses in the data stream by alignment algorithmically the target therein contained with a reference target in a reference stream contained in the memory;

f. rejecting the workpiece if reflectance values in the data stream do not fall with defined limits with the reference stream.

12. A process for video inspection of a workpiece locked on a fixture in an inspection field containing a calibrated gray scale comprising the steps of:

a. viewing the workpiece in a video inspection field containing the calibrated gray scale for reflectance values by video means;

b. transmitting the reflectance values of the workpiece, target and gray scale as addressed analogue signals in a data stream;

c. digitizing the data stream signals;

d. transmitting the digitized data stream to a central processing unit of a computer having a memory and storing the same;

e. correcting the reflectance value of the gray scale in the data stream by comparing it with its equivalent gray scale value in the reference stream and applying the correction to the reflectance values in the data stream;

f. comparing the corrected data stream reflectance values with the reference stream reflectance values;

g. rejecting the workpiece if reflectance values in the data stream do not fall with defined limits with the reference stream.

13. A process for video inspection of a brush locked on a target bearing fixture in an inspection field containing a calibrated gray scale comprising the steps of:

a. viewing the brush in a video inspection field containing the calibrated gray scale and target for reflectance values by video means;

b. transmitting the reflectance values of the brush, target and gray scale as addressed analogue signals in a data stream;

c. digitizing the data stream signals;

d. transmitting the digitized data stream to a central processing unit of a computer having a memory and storing the same;

e. correcting the addresses in the data stream by alignment algorithmically the target therein contained with a reference target in a reference stream contained in the memory;

f. correcting the reflectance value of the gray scale in the data stream by comparing it with its equivalent gray scale value in the reference stream and applying the correction to the reflectance values in the data stream;

g. comparing the corrected data stream reflectance values with the reference stream reflectance values;

h. rejecting the brush if reflectance values in the data stream do not fall with defined limits with the reference stream;

i. accepting the brush of the data stream reflectance values fall within the defined limits of the reference stream.

14. A process for video inspection as in claim 13 wherein the brush is a toothbrush.

15. A process for video inspection of a brush locked on a target bearing fixture in an inspection field comprising the steps of:

a. viewing the brush in a video inspection field containing the target for reflectance values by video means;

b. transmitting the reflectance values of the brush and target as addressed analogue signals in a data stream;

c. digitizing the data stream signals;

d. transmitting the digitized data stream to a central processing unit of a computer having a memory and storing the same;

e. correcting the addresses in the data stream by alignment algorithmically the target therein contained with a reference target in a reference stream contained in the memory;

f. rejecting the brush if reflectance values in the data stream do not fall with defined limits with the reference stream.

16. A process for video inspection as in claim 15 wherein the brush is a toothbrush.

17. A process for video inspection of a brush locked on a fixture in an inspection field containing a calibrated gray scale comprising the steps of:

a. viewing the brush in a video inspection field containing the calibrated gray scale for reflectance values by video means;

b. transmitting the reflectance values of the brush, target and gray scale as addressed analogue signals in a data stream;

c. digitizing the data stream signals;

d. transmitting the digitized data stream to a central processing unit of a computer having a memory and storing the same;

e. correcting the addresses in the data stream by alignment algorithmically the target therein contained with a reference target in a reference stream contained in the memory;

f. rejecting the brush if reflectance values in the data stream do not fall with defined limits with the reference stream.

18. A process for video inspection as in claim 12 wherein the brush is a toothbrush.

* * * * *